United States Patent [19]

Kloss, Jr.

[11] Patent Number: 4,690,845
[45] Date of Patent: Sep. 1, 1987

[54] METHOD AND APPARATUS FOR LAMINATING FLEXIBLE PRINTED CIRCUITS

[75] Inventor: Thomas M. Kloss, Jr., Newtown, Pa.

[73] Assignee: Gila River Products, Inc., Chandler, Ariz.

[21] Appl. No.: 793,452

[22] Filed: Oct. 28, 1985

Related U.S. Application Data

[63] Continuation of Ser. No. 582,303, Feb. 22, 1984, abandoned.

[51] Int. Cl.⁴ .................. A61F 13/02; B32B 7/02; B32B 27/00; C09J 7/02
[52] U.S. Cl. .................. 428/40; 428/209; 428/216; 428/352; 428/423.7; 428/901; 428/910
[58] Field of Search .......... 428/40, 209, 216, 901, 428/910, 352, 423.7

[56] References Cited

U.S. PATENT DOCUMENTS

| | | | |
|---|---|---|---|
| 1,851,177 | 5/1932 | Harvey et al. | |
| 3,066,071 | 4/1963 | Preston | 174/117 |
| 3,136,680 | 6/1964 | Hochberg | 161/189 |
| 3,215,574 | 11/1965 | Korb | 156/3 |
| 3,238,078 | 3/1966 | Baldwin | 156/87 |
| 3,303,081 | 2/1967 | Michaelson et al. | 156/219 |
| 3,433,888 | 3/1969 | Tally et al. | 174/685 |
| 3,649,472 | 3/1972 | Degnan et al. | 204/15 |
| 3,700,537 | 10/1972 | Scher | 161/89 |
| 3,701,706 | 10/1972 | Gittings et al. | 156/306 |
| 3,723,220 | 3/1973 | Scher et al. | 156/219 |
| 3,761,338 | 9/1973 | Ungar et al. | 156/219 |
| 3,929,545 | 12/1975 | Van Dyck et al. | 156/220 |
| 3,932,250 | 1/1976 | Sato et al. | 156/213 |
| 3,940,534 | 2/1976 | Fick et al. | 428/910 X |
| 3,960,627 | 6/1976 | Halberschmidt | 156/104 |
| 3,980,016 | 9/1978 | Taylor | 100/295 |
| 4,075,386 | 2/1978 | Willdorf | 428/423.7 X |
| 4,188,714 | 2/1980 | Jean | 29/628 |
| 4,211,603 | 7/1980 | Reed | 156/659.1 |
| 4,224,378 | 9/1980 | Schroeter et al. | 428/412 |
| 4,249,977 | 2/1981 | Bartholomew | 156/288 |
| 4,264,404 | 4/1981 | Giesler | 156/537 |
| 4,282,120 | 8/1981 | Cisterni | 260/17.4 R |
| 4,340,439 | 7/1982 | Giesler | 156/323 |
| 4,350,551 | 9/1982 | Michaelson | 156/245 |
| 4,461,800 | 7/1984 | Tanaka | 428/217 |

OTHER PUBLICATIONS

DuPont DuPont Tedlar PVF Film.
DuPont Bulletin TD-1A, Revised 8/74.
DuPont Bulletin TD-2, Revised 4/82.
DuPont Bulletin TD-3, Revised 6/68.
DuPont Bulletin TD-5, Revised 11/70.
DuPont Bulletin TD-6, Revised 2/74.
DuPont Bulletin TD-14, Revised 11/75.
DuPont Bulletin TD-33.
DuPont Bulletin TD-34, Revised 11/75.
DuPont Bulletin TD-35, Issued 8/79.
DuPont Price List, Eff. 7/1/81.
Lustro Plastics Co. Lustro A150 CoPolyester Plastic Sheeting-Rolls Price List 4/6/81.
Eastman Plastics Materials Bulletin —MB-58D, Kodar A150 CoPolyester, Mar. 1978.
Polymer Industries Technical Information Bulletin, Lamal HSA.
American Hoechst Corporation, Hostaphan Polyester Film, 5000 Series, (Technical Bulletin), 10/79.
Teledyne, Inc. Teledyne Report, Third Quarter 1982.

Primary Examiner—John E. Kittle
Assistant Examiner—Patrick J. Ryan
Attorney, Agent, or Firm—Charles E. Cates; Victor Myer

[57] ABSTRACT

An article of manufacture and method for assisting the lamination of printed circuits in a flat bed press, in which a stratiform sheet has a thermoplastic layer, a polymeric release layer on one side, a polymeric stabilizing layer having a melting point higher than the laminating temperature peak on the other side, both bonded to the middle thermoplastic layer which has a glass transition point lower than the laminating temperature peak, and a melting point higher than the peak, and the sheet is characterized by substantial freedom from creases, trapped gases, and contaminants between the layers, and the improved method useing the stratiform sheet in a flat bed press operation.

15 Claims, 4 Drawing Figures

METHOD AND APPARATUS FOR LAMINATING FLEXIBLE PRINTED CIRCUITS

This application is a continuation of the copending application Ser. No. 06/582,303, filed Feb. 22, 1984, now abandoned.

BACKGROUND OF THE INVENTION

This invention relates to improvements in methods and materials for laminating printed circuits at low pressures on flat bed presses.

In the manufacture of flexible and flat cable circuits, layers of high dielectric strength plastic films with low shrinkage and good stability at high temperatures are first combined with copper or other conductive metal by an additive or substractive process and electrical circuits are produced by etching or deposition of these metals on the plastic surface. These circuits are then covered by a layer of similar adhesive coated plastic dielectric film to protect and insulate the finished circuit. Holes may be punched or drilled in the layers to allow for connections to the finished circuit.

The circuit assembly is then laid up with a protective cap in single or multiple layers (up to 20 plus) and then laminated under heat (ambient - 400° F.) and pressure (250 to 400 p.s.i.) taking extreme care to register the circuits and drilled holes. This process is normally performed in a flat bed laminating press by the operator of the press, using pad materials consisting of multiple layers piled on between the steel caul plates and the finished circuit. Typically, the first layer, next to the steel plate, is a non-sticking release material such as a tetrafluoroethylene coated fiberglass cloth. The second layer includes multiple plies of kraft paper or equivalent cellulosic wood product; the third layer consists of one or more plies of a thermoplastic film; and the final layer consists of one or more layers of release materials such as tetrafluoroethylene or polyvinyl fluoride.

The resultant lamelliform pad may include 10 or more loosely piled layers of dissimilar materials, each having two sides presenting up to 20 opportunities for possible contamination. Because each layer is customarily handcut and laid up by hand, there is a high margin for error in the sequencing of dissimilar materials, resulting in defective circuits.

The pads are arranged in a prescribed order on either side of the circuit assembly with the release layer facing the assembly. Multiple circuit assemblies with associated pads are placed in the press to form a book, and the entire book is pressed in one operation to laminate the individual circuit assemblies. When the laminating process is complete the pads are stripped away and the laminated circuit assemblies are removed for further handling.

Among the problems found in the prior art process were erratic results and lamination failures due to errors in selecting and laying up the multiple plies of dissimilar materials, hot spots appearing in the laminate creases, pockets of gas and other contamination trapped in the pad, lateral shifting of the pad materials and the circuit laminate, and moisture absorption by the cellulosic pad.

Accordingly, it is an object of this invention to provide a stratiform sheet, for use in laminating printed circuits, characterized by freedom from included gases, contaminants, and creases.

It is also an object of this invention to provide such a stratiform sheet that achieves substantially more reliable method of preparing the book for the laminating step, and more dependable results.

It is further an object of this invention to provide such a stratiform sheet that achieves more even and rapid heat distribution with uniform pressure to a printed circuit.

It is an additional object of this invention to provide a means for minimizing lateral movement of the components of the book in the laminating process and to provide means and methods of reducing the incidence of rejection of the laminated circuit product due to lamination failures.

Yet another object of this invention is to reduce operator error and increase lamination cycle efficiency.

DEFINITIONS

As used in this specification, "laminating temperature peak" means the highest temperature attained in the book while in the laminating cycle under consideration; "manufacturing cycle time" means the time from beginning the job of laying up the book for the press through the press cycle time; "press cycle time" means the time elapsed from starting the pressing operation on the book until the time the book is removed from the press to make room for a new book; "melting point" means the transition from solid including glass to liquid; "glass transition point" means the transition between crystalline to plastic (but not liquid) forms.

SUMMARY OF THE INVENTION

Briefly there is provided to achieve the foregoing objects a stratiform sheet useful in a flat press method of laminating printed circuits. The sheet has a polymeric thermoplastic layer having a glass transition point lower than the laminating temperature peak, and a melting point higher than the laminating temperature peak, a polymeric release layer bonded to a first side of the thermoplastic layer, and a polymeric stabilizing layer, having a melting point higher than, and structural integrity at, the laminating temperature peak bonded to the second side of the thermoplastic layer, and means for joining the layers to unite them into a single, stratiform sheet. The sheet is further characterized by freedom from creases, trapped gases and contaminants between the layers of the sheet.

The polymeric thermoplastic layer may be selected from polyesters, polyvinylchlorides, polyethylenes, polycarbonates, acrylics, ABS and co-polymers of the forgoing materials, in thicknesses ranging from about 4 to 15 mils, preferably about 7.5 mils, and having a glass transition point preferably from about 170° to 225° F.

The polmeric release layer is selected from polyvinylfluorides, polytetrafluoroethylenes, polysiloxanes and other polymers with similar release properties, with a thickness from about 0.1 mil to 4 mils.

The polymeric stabilizing layer is selected from polyimides, polyesters, polyethersulfones, and preferably, biaxially oriented polyethyleneterephthalates, in thicknesses from about 0.5 to 5 mils, preferably, up to about 0.25 to 5 mils. The means for joining the layers of the sheet may be extrusion laminating with thermoplastic polymers such as polyethylene or a urethane prepolymeric type adhesive dissolved in suitable solvents, varying in thickness from 0.1 mil to 1.5 mil.

As further assistance, means are provided whereby the release layer side and the stabilizing layer side may be distinguished.

The stratiform sheet is utilized in the method of laminating printed circuits in a flat press by providing a work piece comprising one or more circuit assemblies in need of lamination, providing the stratiform sheets herein specified, and arranging each circuit assembly in a book with one of said stratiform sheets on each side of a circuit assembly with the release layers thereof facing the circuit assemblies in the press, then pressing the book for the press cycle time appropriate to the product and thickness of the book. The method is particularly useful in press cycles using temperatures up to about 400° F. and at pressures about 250 to 400 p.s.i. in making flexible printed circuits.

BRIEF DESCRIPTION OF THE DRAWINGS

Turning now to the drawings in which a typical prior art book and a presently preferred embodiment of the improvements of this invention are represented.

DESCRIPTION OF THE PREFERRED EMBODIMENT

Figure 1:
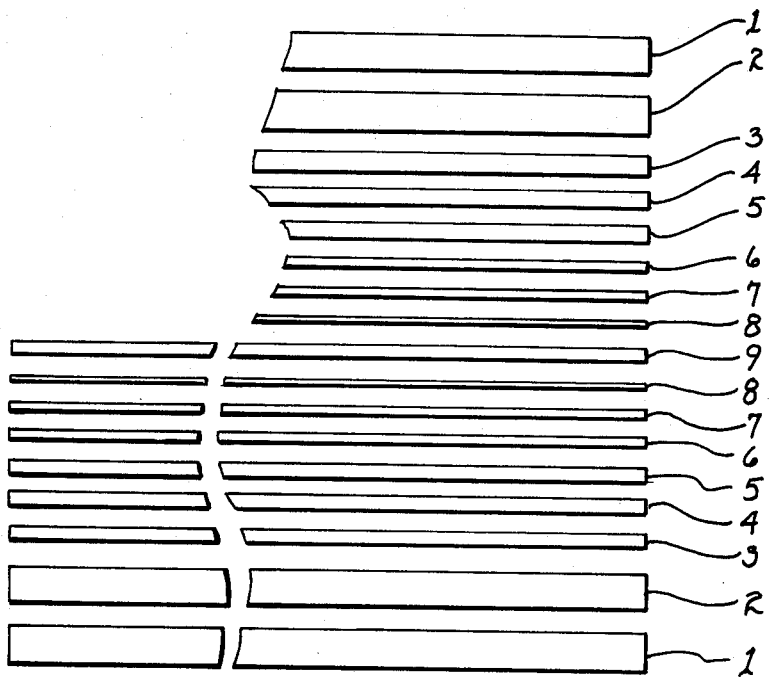
FIG. 1 is a schematic representation of the layering of a book for a flat press, including a single flexible printed circuit assembly and a lamelliform pad, by means of the prior art method.

FIG. 1 represents the standard flexible printed circuit industry approach to preparing a book including a flexible printed circuit (a product particularly suited to use of the invention herein) to be laminated in a flat bed press. Between the press platens typically there are disposed, in the following order from top to bottom, a steel-press plate 1, teflon glass cloth 2, multiple layers of kraft paper 3, 4, 5 a four-mil layer of polyethylene 6, a second four-mil layer of polyethylene 7 and a two-mil release film 8 to make a cushion assembly. Then the flexible circuit assembly 9 is inserted and a mirror image (i.e., reverse order) of the arrangement is repeated on the other side of the circuit assembly. The component parts of the flexible printed circuit product, per se, are not shown, it being understood stood that any suitable flexible, printed circuit assembly to be laminated may become the work piece under consideration.

Multiple stacks of the arrangement between the commonly used glass cloth elements are made to create a book, normally separated by steel plates, and the multiple assemblies are laminated in one pressing.

Many opportunities for error are encountered by press operators in putting together the many layers involved. Errors in selection and sequence of materials are found to be committed by experienced operators. Contamination of the layers is a common hazard. Assembling the layers by hand may cause creases and create gas pockets. The uneven texture of the cellulosic materials causes hot spots, and the rate of heat distribution and transfer is undesirably low.

Figure 2:
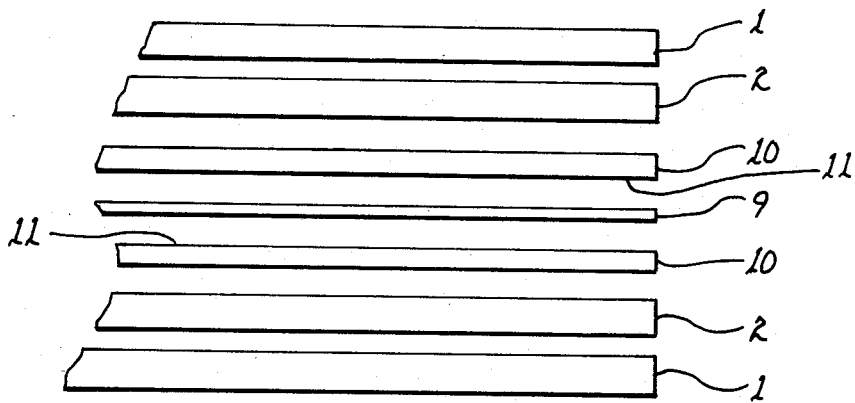
FIG. 2 is a schematic representation of the arrangement of a book including a single flexible circuit assembly and the stratiform sheet means according to this invention.

Attention is now invited to FIG. 2 wherein a presently preferred embodiment of the improved method and product of this invention are shown: As seen in FIG. 2, the platen 1 and the teflon glass cloth 2 are positioned as in the prior art method, but the elements 3 through 8 of the prior art are replaced in their entirety by a single, unitized laminate pad which is herein referred to as a stratiform sheet 10. The flexible printed circuit assembly 9 (the work piece) is the same. A sheet 10, reversed, is positioned on the second side of the flexible circuit assembly followed by the teflon glass cloth 2 and the steel plate 1 to complete the book. The release layer side 11 of each sheet 10 faces the assembly 9. As in the prior art process, multiple flexible circuit assemblies and pads with additional steel plates are stacked between the two layers of glass cloth 2 to make a complete book to charge the press plate in readiness for laminating.

Figure 3:
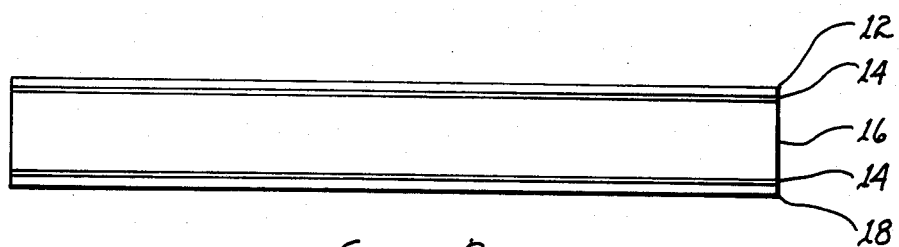
FIG. 3 shows a stratiform sheet made according to the teachings of this invention.

Turning now to FIG. 3, in which an enlarged representation of the pad 10 is shown, layer 12 is a polymeric release layer such as polyvinylfluoride which can be obtained from DuPont Chemical Company under the trademark TEDLAR 50AM20LH, which is the presently preferred polymeric release layer. Other suitable materials are polytetrafluoroethylene, which can be obtained from the DuPont Chemical under the name TEFLON, polysiloxane (silicone) and other polymers with similar release properties. The thickness of layer 12 may vary from 0.1 mil to 4 mils. At more than 4 mils difficulty in conforming to three dimensional products may be experienced.

Layer 14 is a high performance, high temperature adhesive. A presently preferred adhesive may be obtained from Morton Chemical Company under the name LAMAL HSA. It is a two-part urethane, prepolymeric adhesive having a solids content of about 70%, dissolved in isopropanol.

Layer 16 is a polymeric thermoplastic layer which is plastic but not melted, and has good conformability at operating temperatures. The presently preferred thermoplastic is a modified polyester in a thickness of 7.5 mils which is a co-polyester formed from teraphthalic acid and isophthalic acid with cyclohexanedimethanol, and which has a glass transition point about 189° F. It may be obtained from Lustro Plastics Co., Saugus, Calif., under the from Lustro Plastics Co., Saugus, California, under the designation "A150".

Another layer of adhesive 14 is applied to bond the thermoplastic layer 16 and the polymeric stabilizing layer 18.

Layer 18 is a high temperature polymeric layer that remains stable and retains its chemical and dimensional stability at temperatures above the laminating temperature peak. The melting point is 429° F. The presently preferred material is biaxially oriented, polyethyleneteraphthalate made by American Hoechst Corporation under the mark Hostaphan 5000 in thicknesses about 0.25 to 1.4 mil. The function of this layer is to prevent significant lateral movement of the thermoplastic layer 16 when it is in a plastic state.

The function of the thermoplastic layer 16 is to transmit pressure uniformly from the smooth platen to the three dimensional laminate under the conditions of temperature and pressure used to consolidate the laminate. It is necessary that all parts of the encapsulated printed circuit be in intimate contact with the thermosetting plastic (dielectric) which encapsulates it, and that there be no voids or unbonded areas between the circuit and the plastic (dielectric).

A facet of the problem is that if the thermoplastic forming polymer melts and flows freely it may encapsulate and seal the entire book of laminates. According to the practice of this invention, the material selected for layers 16 and 18 will have a melting point above the laminating temperature peak to avoid the liquid state of laminating process temperatures during the press cycle.

If the melt reduces the thermoplastic layer to a thickness that is thinner than the differences between the peaks and valleys in the cross-section of the three dimensional flexible printed circuit the thermoplastic layer loses its ability to conform to the profile of the circuit, and thereby fails in its function of evenly distributing heat and pressure.

Fortuitously, it was discovered that the stabilizing layer solved other problems such as hot spots and poor thermal transmission in the cellulosic material of the prior method.

Normally the laminating cycle is operated at low pressures for no more than a one hour cycle time, but in some cases the cycle time is substantially longer. In such case a polymer that has longer stability at that operating temperature may be selected for layer 18. A polymer made by DuPont Chemical Company under the trademark Kapton is suitable for the longer cycle time. Other considerations are that the polymers selected should be non-reactive, and that the materials have stability at operating temperatures, to avoid chemical breakdown and significant loss of mechanical properties due to thermal degradation. Other suitable polymers are obtainable from ICI Chemical Company under the trademark Melinex, and from American Hoechst Corporation under the trademark Hostaphan and from DuPont under the trademark Mylar.

Among the other benefits obtained from use of the stratiform sheet of this invention there have been found an absence of creases, entrapped gases and other contaminants, shrinkage is minimized, and a more uniform distribution of heat and pressure is maintained throughout the laminating cycle wherein the thermoplastic layer goes through its glass transition stage and back, attributable, it is thought, to the quick initial conformance with pressure and continued conformance with flow in the thermoplastic layer. The results obtained from the product and method of this invention are more reliable, due to the combination of materials and reduction of operator error.

The use of kraft paper is avoided altogether and, fortuitously, materials have been provided in the preferred embodiment that will cover a broad range of pressing conditions and most of the pressing requirements encountered in the flexible printed circuit art.

As will be explained in greater detail hereafter the stratiform sheets are made by continuous roller process laminating with heat and pressure, whereby the layers of the stratiform sheet are cemented together by adhesives and are rolled and smoothed to make intimate contact, one layer to another, resulting in an absence of air pockets and creases. The process is carried out in a clean room which produces a contamination free product.

Manufacture of Stratiform Sheet Material

The stratiform sheet material of this invention is manufactured on a continuous web laminating system wherein a suitable adhesive is applied to a roll of the thermoplastic material. It is then passed through an oven to remove the solvent and a release layer is applied to the adhesive layer using a heated nip and the resulting laminate is reversed and suitable adhesive is applied to the other side of the thermoplastic layer. It goes through the oven to remove the solvent, and the stabilizing layer is applied to the second adhesive treated side using a heated laminating nip and the continuous sheeting is collected on another roll. From there it may be cut to specifically desired sizes suitable for immediate insertion into a book for use in a press, or it may be shipped in roll form to a remote location for processing in that manner. An example of the manufacture of the invention follows.

EXAMPLE I

To a roll of a co-polyester formed from terephthalic acid and isophthalic acid with cyclohexanedimethanol and whose glass transition point is 189° F. and whose sheet thickness is 7.5 mils (obtained from Lustro Plastics Co., Saugus, Calif. under its designation A150) there was applied a two-part urethane prepolymeric adhesive (obtained from Morton Chemical Company under the name Lamal HSA) by means of a standard gravure coating head. The coated co-polymer was sent through an oven to remove the solvents from the adhesive and a roll of polyvinylfluoride (obtained from DuPont Chemical Company under the brand name TEDLAR 50AM20LH) was laminated to the adhesive-treated side with a hot laminating nip and collected on a second roll.

The second roll was passed through the gravure apparatus again to apply the Lamal adhesive to the opposite side of the A150 co-polymer. The coated sheet was again passed through the oven to remove the solvents and laminated to a roll of polyethyleneteraphthalate (obtained from American Hoechst Company, trademarked Hostaphan 5000), through a hot laminating nip. The resulting stratiform sheet was collected on a roll for storage. At a subsequent time it was formed into pads of a suitable size for inclusion in a book of flexible printed circuit laminates for processing in a flat bed press.

Optionally, the means of manufacture might be a one pass coating operation, and be done with a variety of coating methods such as, for example, Meyer rod, air knife or reverse roll coating offset gravure.

Method of Use of the Stratiform Sheet

The stratiform sheet of this invention replaces multiple layers of dissimilar materials used in the flat bed press method of forming flexible printed circuits under low pressure and heat. Whereas, formerly, the press operator was obliged to cut and lay up as many as 20 different layers of paper and plastic materials in the method of this invention, a single stratiform sheet placed on each side of the circuit assembly will suffice.

In the method of this invention, which is particularly useful in laminating flexible printed circuits in a flat bed press, one or more circuit assemblies are provided as a work piece, a single stratiform sheet is arranged on each side of a circuit assembly with the release layer of each sheet facing a circuit assembly in the press. The book of as many circuit assemblies as desired is arranged in the press between teflon glass cloth layers and steel press plates at each end and between each repetition of circuit assembly and associated stratiform sheets. The book is then pressed at temperatures ranging from room temperature up to about 400° F., typically about 350°–380° F. and at pressures between 250–400 p.s.i.

Some of the advantages enjoyed by use of the method utilizing the stratiform sheet is that the time consuming chores of cutting and sequencing the layers at the press are entirely eliminated, resulting in a shorter manufacturing cycle time. The human error encountered in cutting and putting the layers together is avoided and consequently the chances of ruining an expensive work piece is almost entirely eliminated.

Identifying indicia are provided as matte surface on one side of the sheet and smooth on the other side.

Examples of the use of product and method of this invention follow.

EXAMPLE II

A book for press lamination is made up of caul plate, glass cloth, a stratiform sheet of this invention, flexible circuit assembly in need of lamination, stratiform sheet, glass cloth and caul plate, in that order, with the release layers of the stratiform sheets facing the circuit assembly.

A typical circuit assembly was used as the work piece. The stratiform sheet is provided with matte finish on the release layer side and smooth finish on the stabilizing layer side.

The book is assembled at the press site and loaded to a flat bed laminating press. The press cycle is carried out for 80 minutes at 300 p.s.i. The laminating temperature peak is 360° F. Table 1 is a tabulation of temperature progression against time.

The work piece is removed from the press. Upon examination it is found to be well formed and free of defects.

EXAMPLE III

To compare the results of the method and product of the invention with the prior art, another run was made using the same circuit assembly as in Example II and a cushion assembled according to present industry practices as illustrated in FIG. 1 of the drawings.

The time versus temperature results from Example III are shown in Table 2.

Figure 4:
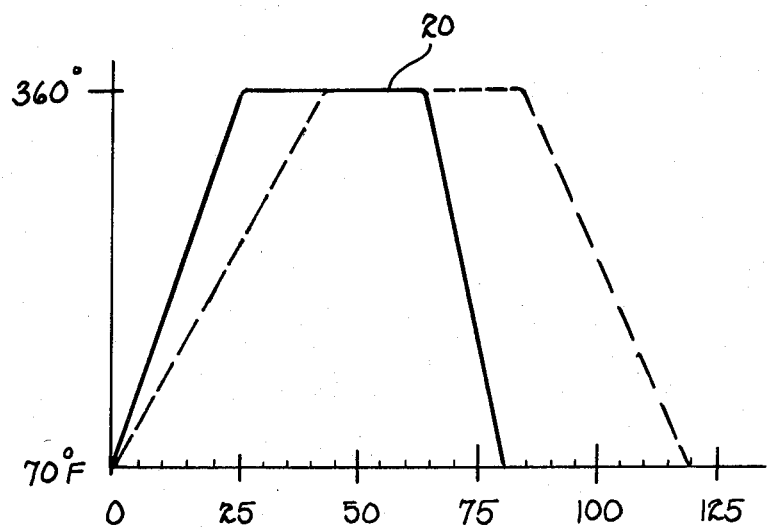
FIG. 4 shows the temperature curve in a typical prior art press cycle and the contrasting temperature curve in a press cycle utilizing this invention.

The combined data are plotted on the time versus temperature curves in FIG. 4 of the drawings.

TABLE 1

| Time: | 0 | 25 min. | 65 min. | 80 min. |
|---|---|---|---|---|
| Temp: | 70° F. | 360° | 360° | 70° |

TABLE 2

| Time: | 0 | 45 min. | 85 min. | 120 min. |
|---|---|---|---|---|
| Temp: | 70° F. | 360° | 360° | 70° |

Because there is no longer a need for purchasing dissimilar materials and storing them at the plant, the logistics of purchasing, transporting, collecting and storing multiple inventories are simplified, with a consequent savings of time and money and space. Greater consistency in the pressing process is obtained by using certain materials. In the stratiform sheets of this invention the materials have been selected to cover a broad range of circuit design requirements thereby reducing the need for ad hoc selections of materials for laminating flexible printed circuits. Furthermore, the floor space now required in the prior art for cutting, assembling and storing the pads at or near the press site (after the materials are removed from the warehouse) has also been avoided.

What is claimed is:

1. A stratiform press sheet for use in laminating three dimensional flexible printed circuits on a flat bed press, said press sheet having its component layers bonded together to form a unified sheet containing:

(a) a median layer comprising a polymeric thermoplastic film having a glass transition point lower than the laminating temperature peak, a melting point higher than the laminating temperature peak, and a thickness at the laminating temperature peak at least as great as the differences between the peaks and valleys in the cross-section of the three-dimensional flexible printed circuit for uniform transmission of pressure in said laminating process;

(b) a polymeric release layer having a thickness of from 0.1 to 4 mils and having an outer surface for releasable disposition against a printed circuit which is being laminated;

(c) an outer polymeric stabilizing layer having a melting point higher than the laminating temperature peak and being formed as an integral part of said unified press sheet in order to prevent lateral movement of said thermoplastic film when in a plastic state in said laminating process; and (d) adhesive means to bond the component layers in a single, stratiform press sheet, said press sheet being further characterized by substantial freedom from creases, entrapped gases, and contaminants between said layers.

2. A charge of material for a flat bed press useful in printed circuit lamination comprising a printed circuit assembly and a separate unified stratiform press sheet containing:

(a) a polymeric release film layer having a thickness of 0.1 to 4 mils and having an outer surface for releasable disposition against a printed circuit to be laminated;

(b) an inner layer comprising a thermoplastic ploymeric film having a glass transition point lower than the laminating temperature peak and a melting point higher than the laminating temperature peak for uniform transmission of pressure in said printed circuit lamination;

(c) an outer polymeric stabilizing layer having a melting point higher than the laminating temperature peak and being formed as an integral part of said unified press sheet in order to prevent lateral movement of said thermoplastic film when in a plastic state in said laminating process; and (d) adhesive means to bind the component layers in a single, stratiform press sheet, said stratiform sheet being further characterized by substantial absence of creases, gases and contaminants between said layers.

3. A separate stratiform press sheet useful in assisting the process of heat forming laminated flexible printed circuits on a flat bed press at low pressure, comprising:

(a) an outer stabilizing layer of plastic film for preventing lateral movement of a thermoplastic layer when bonded thereto, selected from polyesters, polyethersulfones, polyimides, and biaxially oriented polyethyleneterephthalates which have melting points higher than the laminating temperature peak, in thicknesses from about 0.25 to 5 mils;

(b) a temperature responsive median layer of plastic film for uniform transmission of pressure in said process of heat forming flexible printed circuits selected from polyvinylchloride, polyethylenes, polycarbonates, acrylics, ABS, polyesters, and co-polymers thereof, in thickness thereof from about 4 mils and 15 mils and having a glass transition point lower than the lamination temperature peak;

(c) an inner release film selected from polyvinylfluorides, polytetrafluoroethylenes and polysiloxanes in thicknesses from about 0.1 to 4 mils; and (d) means for bonding the components of said press sheet, selected from compatible polymeric adhesives.

4. The stratiform press sheet of claim 1 wherein said polymeric thermoplastic layer is selected from polyvinylchlorides, polyethylenes, polycarbonates, acrylics, ABS, polyester and co-polymers thereof; said polymeric release layer is selected from polyvinylfluorides, polytetrafluoroethylenes, and polysiloxanes, in a thickness from 0.1 mil to 4 mils, and said polymeric stabilizing layer is selected from polyesters, polyethersulfones, biaxially oriented polyethyleneterephthalates and polyimides.

5. The stratiform press sheet of claim 1 wherein the polymeric release layer and the polymeric stabilizing layer are joined to the polymeric thermoplastic layer by means of polymeric adhesives.

6. The stratiform press sheet of claim 5 wherein said adhesive is a two-part urethane prepolymeric adhesive.

7. The stratiform press sheet of claim 1 wherein said films are bonded to each other with an adhesvie comprising a thermoplastic resin selected from extrudable polyethylene and polypropylene.

8. The stratiform press sheet of claim 1 wherein the means for joining said layers is by extrusion lamination with thermoplastic polymers.

9. The stratiform press sheet of claim 1 with the addition of identifying indicia for distinguishing the release layer side from the stabilizing layer side to prevent inadvertent reversal in use.

10. The stratiform press sheet of claim 1 wherein the glass transition point of said thermoplastic polymer is from about 170° F. to about 225° F.

11. The charge of material of claim 2 wherein the glass transition point of said thermoplastic polymer is from about 170° F. to about 225° F.

12. The stratiform press sheet of claim 1 wherein the glass transition point of said thermoplastic layer is about 189° F.

13. The charge of material of claim 2 wherein the glass transition point of said thermoplastic layer is about 189° F.

14. The separate stratiform press sheet of claim 3 wherein said outer layer is a biaxially oriented polyethyleneterephthalate, said inner layer is polyvinylfluoride, said median layer is a co-polyester formed from terephthalic acid and isophthalic acid with cyclohexanedimethanol in a thickness of 7.5 mils and said adhesive is a two-part urethane prepolymeric adhesive.

15. The separate stratiform sheet of claim 3 wherein means are provided for distinguishing the outer and inner layers thereof, said means comprising a smooth finish on one side of said sheet and a matte finish on the other side of said sheet.

* * * * *